(12) United States Patent
Sattar et al.

(10) Patent No.: US 7,211,428 B1
(45) Date of Patent: May 1, 2007

(54) **STRAIN OF *BACILLUS* AS A BIOINOCULANT**

(75) Inventors: Abdul Sattar, Lucknow (IN); Mansoor Alam, Lucknow (IN); Abdul Khaliq, Lucknow (IN); Suman Preet Singh Khanuja, Lucknow (IN); Alok Kalra, Lucknow (IN); Abdul Samad, Lucknow (IN); Ajit Kumar Shasany, Lucknow (IN); Mahendra Pandurang Darokar, Lucknow (IN); Ashutosh Kumar Shukla, Lucknow (IN); Togarati Padmapriya, Lucknow (IN); Mohammad Yaseen, Lucknow (IN); Om Parkash Dhawan, Lucknow (IN); Mohammad Zaim, Lucknow (IN); Poovappallivadakethil Viswanathan Nair Ajaya Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 186 days.

(21) Appl. No.: 10/847,623

(22) Filed: May 18, 2004

(51) Int. Cl.
*C12N 1/20* (2006.01)
(52) U.S. Cl. .................................. 435/252.5; 435/832
(58) Field of Classification Search ............. 435/252.5, 435/832
See application file for complete search history.

(56) References Cited

U.S. PATENT DOCUMENTS 5,344,647 A * 9/1994 Rossall .................. 424/93.462
6,896,883 B2 * 5/2005 Bergstrom et al. ..... 424/93.462

* cited by examiner

*Primary Examiner*—Vera Afremova
(74) *Attorney, Agent, or Firm*—Sughrue Mion, PLLC

(57) ABSTRACT

The present invention relates to the selection and development of superior strain of *Bacillus* spp for improving plant growth and health by inhibiting pathogenic fungi.

1 Claim, No Drawings

STRAIN OF *BACILLUS* AS A BIOINOCULANT

FIELD OF INVENTION

The present invention relates to the selection and development of superior strain of *Bacillus* spp for improving plant growth and health by inhibiting pathogenic fungi

BACKGROUND OF INVENTION

Crops under cultivation suffer from many diseases caused by plant pathogenic fungi. One particularly damaging plant phytopathogenic fungus is *Rhizoctonia solani* which is widely distributed and causing common diseases of greenhouse-grown crops, field crops, vegetables, ornamentals, and fruits throughout the world. It also causes root rot and wilt disease of pyrethrum and geranium. Other detrimental fungal plant pathogens include *Sclerotinia sclerotiorum, Thielavia basicola, Fusarium oxysporum*, causing wilt, *Pythium aphanidermatum* causing lethal yellowing and damping off in numerous plants.

The incidence of various kinds of fungal diseases cause considerable damage to the medicinal and aromatic plants (MAPS) in different part of India. The occurrence in severe form may either kill emerging seedlings or reduce plant growth and adversely affect the crop yield. Among fungal pathogens, species of *Rhizoctonia, Sclerotinia, Fusarium, Thielavia, Pythium, Helminthosporium, Curvularia, Alternaria* and *Colletotrichum* are most important and common. They produce different kinds of diseases such as stem rot and twig blight (*Sclerotinia sclerotiorum*) on periwinkle, Egyptian henbane and *Ammi majus*; root rot & wilt (*Rhizoctonia solani*) diseases on pyrethrum, leaf blight (*Curvularia andropogonis*); lethal yellowing (*Pythium aphanidermatum*) and collar rot (*Fusarium moniliforme*) on Java citronella; damping-off (*Pythium dissotocum*), collar rot (*Rhizoctonia solani*) and leaf blight (*Alternaria alternata*) on opium poppy, stolon and root rot (*Thielavia basicola*), wilt (*Fusarium oxysporum*), leaf blight (*Corynespora cassiicola*) on mints and anthracnose (*Colletotrichum acutatum*) and wilt (*Rhizoctonia solani*) on geranium; (Alam et al 1983, Indian Phytopath. 367: 480–483; ibid 1992, Plant Disease 43:10578–1061; ibid 1994, Plant Pathology 43:1057–1061; ibid 1996, Indian Phytopath. 49:94–97; Sattar et al. 1993, Indian J. Plant Pathol 10: 10–11; ibid 1999, Indian J. Plant Pathol. 17:74–76; ibid 2002, J. Mycol. & Pl. Pathol. 32: 31–34).

The use of huge amount of fertilizers and chemical pesticides for maintaining the high productivity of crop has become fatal to human and animal health. They also poses many other serious problems including i) development of resistant strains of pathogen (Schwinn et al., (1991) "Control with Chemicals" Advances in Plant Pathology: vol. 7: *Phytophtohora infestans*, the Cause of Late Blight of Potato, Ingram et al., eds., Academic Press, 8: 255–266) ii) build up of harmful residues in the edible plant and iii) non-target side effect of beneficial micro flora. It is desirable to replace them with biopesticides derived from the microorganisms. They are as effective as broad-spectrum chemical pesticides, easily degradable and have low cost production. They are a distinct possibility for the future and can be successfully exploited in modern agriculture without affecting our precious ecosystem.

Plant growth promoting rhizobacteria (PGPR) exert a beneficial effect on the plant by causing plant growth promotion and/or suppressing plant pathogen population to avoid infection. Efforts to select and apply PGPR for control of specific soilborne fungal pathogens have been reviewed (Kloepper, 1993; Glick and Bashan, 1997 Biotechnology Advances 15, 353–378). In most of the cases, activity is due to production of metabolites such as antibiotics, hydrogen cyanide, iron-chelating siderophores, and cell wall-degrading enzymes, which directly inhibit the pathogen. Plant growth promotion by PGPR may also be an indirect mechanism leading to a reduction in the probability of a plant contracting a disease when the growth promotion results in shortening the time that a plant is in a susceptible state. An alternative mechanism for biological control by PGPR is by induced systemic resistance.

*Bacillus subtilis* and few other *Bacillus* spp. are used as biocontrol agents of fungal diseases caused by different plant pathogens (Swinburne et al. (1975) Trans. Brit. Mycol. Soc. 65:211–217, Baker et al. (1983) Phytopathology 73:1148–1152, Singh and Deverall, (1984) Trans. Br. Mycol. Soc. 83:487–490, Cook (1987) Proceedings Beltwide Cotton Production—Mechanization Research Conference, Cotton Council, Memphis, pp. 43–45, Gueldner, et al., (1988) J. Agric. Food Chem. 36:366–370, Pusey et al. (1988) Plant Dis. 72:622–626, Ferreira et al. (1991) Phytopathology 81:283–287, Sholberg et al. (1995) Can. J. Microbiol. 41:247–252, Asaka, and Shoda, (1996), Appl. Environ. Microbiol. 62:4081–4085). McKeen et al. (1986) Phytopathology 76:136–139 and Pusey and Robins (1991) U.S. Pat. No. 5,047,239 disclose control of post harvest fruit rot using *B. subtilis*. Among different *Bacillus* spp (*B. subtilis, B. megaterium B. cereus, B. polymyxa* and *B. pumilus*), *B. subtilis* is most exploited as biocontrol agent because it is considered to be a safe and potential biological control agent due to high thermal tolerance, rapid growth in liquid culture, ready formation of resistant spores. Handelsman (1991) U.S. Pat. No. 5,049,379 disclose that Zwittermicin-A producing *B. cereus* control damping off in alfalfa and soybeans by inhibiting root rot fungus. A *Bacillus subtilis* GBO3 strain is commercially used as seed dresser under the names KODIAC.™. HB. or GUS 2000.™. by Gustafson, Inc. Plano, Tex. 75093 (EPA Reg. No. 7501–146, 1992). This product is available as a 2.75% powder formulation containing not less than 5.5.times10. sup. 10 viable spores per gram and is to be applied at a rate ranging from 2–4 ounces per 100 pound of seed. The bacteria is said to colonize the developing root systems and compete with pathogens that would attack the roots. Huang et. al (1993), Can. J. Microbiol. 39: 227–233 investigated antagonistic behavior of two strains of *Bacillus cereus*; alf-87A & B-43 against *Sclerotinia sclerotiorum*, the causal agent of basal pod rot & end rot disease on dry pea. The vegetative growth & ascosporic germination of *S. sclerotiorum* are inhibited by diffusible metabolite produced by alf-87A but are unaffected by strain B-43 The spraying on pea plants at the pod development stage with alf-87A reduce the incidence of basal rot. The treatment of soybeans with *B. cereus* has been shown to improve soybean yield at field site (Osburn et al. 1995 Am. Phytopathol. Soc. 79: 551–556). Chen et al (2002) Chinese J. Biol. Control 18:45–46 report that antagonistic activity of B-916 strain of *B. subtilis* against *R. solani* is due to proteins because addition of ammonium sulphate in culture solution destroys its antagonistic ability. The application of *B. subtilis* reduced the stem canker disease caused by *R. solani* and common scab disease caused by *Streptomyces* scabies up to 63% and 70%, respectively. Liu et al. (1995) U.S. Pat. No. 5,403,583 disclosed a *Bacillus* sp., ATCC 55000 and a method to control the fungal plant pathogen, *Rhizoctonia solani*. Leifert et al. (1995), J. Appl Bacteriol. 78:97–108, reported the production of anti-*Botrytis* and anti-*Alternaria* antibiotics by two *Bacillus* strains, *B. subtilis* CL27 and *B. pumilus* CL 45. The whole broth and cell-free filtrates were active against *Botrytis* and *Alternaria* in in vitro tests and were active against *Botrytis* in in vivo small plant tests. Leifert et al. (1997) U.S. Pat. No. 5,597,565 disclosed that *B. subtilis, B. pumilus* and *B. polymyxa* are effective against post harvest disease caused by *Alternaria brassicicola* and *Botrytis cinerea*. They also disclose the presence of antibiotics produced in the cell-free culture filtrate and their activity at different pH values, but they do not identify these compounds. The compounds from *B. subtilis* lose activity at low pH, while the activity from the *B. pumilus* extracts occurs only at pH values below 5.6. Leifert, et al. (1998) U.S. Pat. No. 5,780,080 disclose that the growth of *Botrytis cinerea* and *Alternaria brassicicola* causing post-harvest disease is inhibited by applying isolates of *Bacillus pumilus* NCIMB 40489 and *Bacillus subtilis* NCIMB 40491 to cabbage at temperatures of about 20.degree C.

Bacilli are known to produce antifungal and antibacterial secondary metabolites (Korzybski, et al., 1978 "Section C: Antibiotic isolated from the genus *Bacillus* (Bacilliaceae)" In: Antibiotics—Origin, nature and properties, American Society for Microbiology, Washington D.C. Vol. III, pp. 1519–1661). The chemical nature of antibiotics produced by *Bacillus* spp. are peptide by the action of which they inhibit the growth of fungal plant pathogens in the microenvironment (Katz and Demain 1977 Bacteriological Reviews, 41, 449–474; Singh & Deveral 1984; McKeen et al. 1986; Utkhede et al (1986) Can. J. Microbiol. 32: 963–967; Wilson et al. (1989) Annual Review of Phytopathology. 27, 425–441, Hiraoka et al., (1992) J. Gen. Appl. Microbiol. 38:635–640.). Islam and Nandi (1985) J. Plant Dis. Protect. 92:241–246, disclose a *Bacillus* sp. with antagonism to *Drechslera oryzae*, the causal agent of rice brown spot. The same authors, Islam and Nandi (1985) J. Plant Dis. Protect. 92(3):233–240, also disclose in-vitro antagonism of *Bacillus* sp. against *Drechslera oryzae, Alternaria alternata* and *Fusarium roseum*. They discussed three components in the culture filtrate. The most active antibiotic was highly soluble in water and methanol with a UV peak at 255 nm and a shoulder at 260 nm, that proved to be a polyoxin-like lipopeptide. Loeffler et al. (1986) J. Phytopathology 115: 204–213, disclose *B. subtilis, B. pumilus, B. licheniformis,* and *B. coagulans* strains that produce various antibiotics with antifungal and antibacterial activity. *B. pumilus* produces bacilysin and iturin A. Bacilysin is a very small compound with a molecular weight of 270, that inhibits only yeast. The iturins, which are soluble in polar solvents, have broad antifungal and antibacterial activity. McKeen et al. (1986), have shown that antibiotics similar to the low molecular weight iturin cyclic polypeptides contribute to the fungicidal activity of *B. subtilis*. Rossall's (1991) U.S. Pat. No. 5,061,495 provides a novel antibiotic from *B. subtilis* that is 63,500 Dalton, precipitates at a pH below 5 and has activity against gram positive bacteria and fungi (*Botrytis* and *Erysiphe*). Rossall's (1994) U.S. Pat. No. 5,344,647 discloses *Bacillus subtilis* strains with broad anti-fungal activity. Stabb et al. (1994), Applied Environ. Microbiol. 60: 4404–4412 have identified different strains of *B. subtilis, B. cereus, B. mycoides, B. thuringiensis* that exhibit antifungal activity. These strains have been shown to produce zwittermicin-A and/or kanosamine (Milner et al. 1996, Applied Environ. Microbiol. 62: 3061–3066), that are effective against damping off disease caused by *Phytophthora medicagenis, P. nicotianae, Pythium aphanidermatum* or *Sclerotinia minor*. Zwittermicin-A is a water soluble, acid stable linear aminopolyol molecule (He et al. 1994, Tetrahedron Lett. 35: 2499–2502) with broad spectrum activity against many fungal and bacterial plant pathogens. Kanosaminealso inhibits a broad range of fungal plant pathogens and a few bacterial species (Milner et al. 1996).

Germida, et al. U.S. Pat. No. 6,015,553 disclosed *Bacillus subtilis* strain AQ743 that produces a metabolite exhibiting pesticidal activity against corn rootworm. Hassanein and El-Goorani (1992) J. Plant Pathol. 133: 239–246 reported that application of *B. subtilis* on wounded caster bean plants 30 min. before or simultaneously with inoculation of *Agrobacterium tumefaciens*, resulted in good control of crown gall without any phytotoxic injury or growth retarding side effect.

So in the present invention systematic experiments were planned to isolate and select superior strain of *Bacillus* strain for promoting the growth of medicinal and aromatic plants as well as inhibiting the growth of plant pathogenic fungi.

OBJECTS OF THE INVENTION

The main object of the present invention relates a novel strain of *Bacillus* species having Acccession No. MTCC 5130.

Yet another object of the present invention relates to the novel strain as Bioinoculant for plant growth promotion Still another object of the present invention relates to use of bacterial strain for antifungal activities and capability of reducing fungal infection in medicinal and aromatic plants.

Another object of the present invention relates to use of the bacterial strain for the control of fungal diseases selected from root rot and wilt disease.

SUMMARY OF THE INVENTION

The present invention provides a novel and potential strain of *Bacillus* spp, designated herein as *Bacillus* spp strain MTCC 5130, which is highly effective in promoting the growth of a plant and inhibiting the growth of a wide range of plant pathogenic fungi.

The invention provides a composition of a biologically active *Bacillus* spp strain MTCC 5130 in promoting the growth of treated plant and inhibiting the growth of a wide range of plant pathogenic fungi. The composition is effective to promote the growth of pyrethrum and geranium plant and inhibit infection of *Rhizoctonia solani* causing root rot & wilt disease on pyrethrum and geranium plant. The invention also encompasses a method for protecting pyrethrum and geranium plants from root rot and wilt disease caused by *Rhizoctonia solani* by applying to the plant or its environment (rhizosphere).

DETAILED DESCRIPTION OF THE INVENTION

The present invention relates to the selection and development of a superior strain of *Bacillus* spp isolated from a soil at Central Institute of Medicinal and Aromatic Plants (CIMAP), Lucknow, India, where field experiments on geranium (*Pelargonium graveolens*) were conducted. The selected strain improves plant growth and health, particularly geranium and pyrethrum (*Chrysanthemum cinerarifoloum*). Further, the invention is related to inhibition of growth of pathogenic fungi by the newly selected *Bacillus* spp MTCC 5130 strain and has been found to be highly effective in protecting pyrethrum from root rot and wilt disease caused by *Rhizoctonia solani* (PyRh1) and rosescented geranium from wilt disease caused by *Rhizoctonia solani* (GRh1). The invention also includes methods of treatment for the control of root rot and wilt disease in pyrethrum plants by using bacterial strain as such or in delivery medium.

Accordingly, the main embodiment of the present invention relates to a novel *Bacillus* spp bacterial strain having accession No MTCC-5130, deposited at Institute of Microbial Technology, Chandigarh, India, said bacteria having following characteristics:

Morphological Characteristics:
Cell shape: Spherical colonies
Cell size: 2–3 mm
Cell arrangement: rod arrangement
Gram stain: Positive
Motility: Yes
Pigment: Absent
Capsule: Absent
Spores: Endospore formation
Physiological Properties
Behaviour to oxygen: Aerobic or facultative anaerobic
Conditions for growth:
  pH-5.6–6.5
  Temperature –25±2° C.
Biochemical Properties:
Solvent tolerance test: Butanol Positive
Indole test: Negative
Cytochrome oxidase Test: Positive
Growth Under Culture Conditions:
Potato Dextrose Agar (PDA): The bacterial isolate was found to have spherical colonies about 2–3 mm. in diameter, flattened and mucoid in texture. These were gram positive rods. When the staining for endospore formation was carried out the isolate was found to be forming endospores in the centre of the cells. This isolate was found to be similar to *Bacillus* on the basis of endospore position.

Potato Dextrose Broth (PDB) (liquid Medium): The strain grew profusely and sporulated very extensively.

Genotype Characteristics:

DNA was isolated and its nucleotide composition was determined from its melting temperature (91.2° C.). The G+C content was calculated by the equation: % G+C=T-69.107/0.41. The G+C content in the DNA of strain NP1010 was 510.24, a value close to that of *Geobacillus thermoleovorans* (55%).

Amplification and 16S rRNA Gene Sequence Analysis

The partial 16S rRNA gene was amplified, then subjected to cycle sequencing with protocol of MicroSeq 500 Kit procured from Perkin Elmer Applied Bio systems (USA). The amplified product was sequenced using the forward sequencing reaction mix. The DNA sequence was searched for homology using BLAST search engine at NCBI site (ncbi.nlm.nih.gov) and FASTA (ebi.ac.uk). Maximum similarity (E value 2e-11, Score 78) was with Gamma proteobacterium AKB16 16S ribosomal RNA gene, partial sequence (Accession no AY083466.). In the FASTA homology search most of the hits were for *Bacillus* spp in addition to Gamma proteobacteria. The partial rDNA sequencing provided a characteristic 16S rDNA not having complete homology with any bacteria of the database but showed similarity towards Gamma proteobacteria and *Bacillus* spp.

```
                                              (SEQ ID NO:41)
1   TAATGTCGGT GGTGCGTTCA ACATACGTAA GCTAAGTGGA

AAAGACGGGA ATGCCGTCTT TCGACGCCAA GTGGTGGATG

GGCGAGCAAT ATGCGGGCAA TTCGTTCGCA AGATCGGGAC

AATCTTGGGA AATTGGGGTC AACATTGGAC GGCCGCCCGA

ATTGTACGGC CTAAGATACA AAAGGCGGTC CTGGTCATTA

TCCATAGACG GATTTGTGGT GTACCAGTCA GCCGCCGAGG

CAATGGTCTA TTAAGGTAAA GACGTGCAGT TGATTCGAGA

GGGCGACTGG TTATATCGGG ATCGAGATAA TGTTTAAATC

TTCATGGGAG GTAGTAGCAG GGAACTCCTT TTAACCGATT

AAAGCTCCAT TGAGTAATTT TTTTTCAAGC GACCAAGGCC

CCTCGCTTTC AAAGTCTTTC CCCCCCAGGG AAAAATAAAC

GGTGCCCCAA AACAAGGGGG GGATTTCCGT A 471.
```

Another embodiment of the present invention relates to novel *Bacillus* spp bacterial strain having accession No MTCC-5130 capable of enhancing plant growth and inhibiting fungal pathogens infecting the plants.

Another embodiment of the present invention relates to the strain MTCC 5130 wherein said strain has plant growth promoting activity by inhibiting fungal pathogens for medicinal and aromatic plants.

Still another embodiment of the present invention relates to medicinal and aromatic plants wherein the medicinal and aromatic plants are selected from group consisting of *Pelargonium graveolens* and *Chrysanthemum cinerarifolium* and other related aromatic and medicinal plant species.

Yet another embodiment of the present invention relates to fungal pathogens wherein fungal pathogens are selected from group consisting of *Rhizoctonia* spp., *Fusarium* spp., *Pythium* spp., *Helminthosporium* spp., *Curvularia* spp., *Alternaria* spp., *Colletotrichum* spp., *Corynespora* spp, and *Thielavia* spp.

Yet another embodiment of the present invention relates to fungal pathogens wherein fungus pathogens are selected from group consisting of *Rhizoctonia solani*, *Fusarium oxysporum*, *Fusarium semitectum*, *Pythium aphanidermatum*, *Helminthosporium carbonum*, *Curvularia andropogonis*, *Alternaria alternata*, *Colletotrichum acutatum*, *Colletotrichum capsici*, *Colletotrichum gloeosporiodes*, *Corynespora cassiicola*, and *Thielavia basicola*.

Another embodiment of the present invention relates to the inhibition of fungal pathogens by strain wherein strain inhibits *Rhizoctonia solani* inhibited in the range of about by 40–75%, inhibits *Fusarium oxysporum* in the range of about 70 to 80, inhibits *Fusarium semitectum* in the range of about 65 to 75%, inhibits *Pythium aphanidermatum* in the range of about 10–30%, inhibits *Helminthosporium carbonum* in the range of about 50 to 65%, inhibits *Curvularia andropogonis* in the range of about 65 to 80%, inhibits *Alternaria alternata* in the range of about 75 to 90%, inhibits *Colletotrichum acutatum* in the range of about 70–80%, inhibits *Colletotrichum capsici* in the range of about 60–75%, inhibits *Colletotrichum. gloeosporiodes* in the range of about 50–65%, inhibits *Corynespora cassiicola* in the range of about 40–55%, and inhibits *Thielavia basicola* in the range of about 50–65%.

Still another embodiment of the present invention relates to the inhibition of the fungal pathogens wherein inhibition of *Rhizoctonia solani* is about 55%, inhibition of *Fusarium oxysporum* is about 73%, inhibition of *Fusarium semitectum* is 68%, inhibition of *Pythium aphanidermatum* is about 20%, inhibition of *Helminthosporium carbonum* is about 55%, inhibition of *Curvularia andropogonis* is about 70%, inhibition of *Alternaria alternata* is about 83%, inhibition of *Colletotrichum acutatum* is about 76%, inhibition of *Colletotrichum capsici* is about 65%, inhibition of *Colletotrichum. gloeosporiodes* is about 58%, inhibition of *Corynespora cassiicola* is about 48%, and inhibition of *Thielavia basicola* is about 58%.

Yet another embodiment of the present invention relates to the strain wherein said strain is effective in reducing the spore germination of fungal pathogens is in the range of about 90–100%.

One more embodiment of the present invention relates to the spore germination reduction wherein the reduction in spore germination of fungal pathogens is about 95%. Another embodiment of the present invention relates to the strain wherein strain MTCC 5130 is effective in increasing the plant yield in the range of about 90–100%.

Still another embodiment of the present invention relates to the strain MTCC-5130 wherein said strain is effective in increasing the plant yield by about 95%.

Yet another embodiment of the present invention relates to the strain MTCC 5130 wherein said strain is effective in enhancing the yield of plant in the range of about 290 to 370 g/pot herb yield when used alone or in combination with other bioinoculants.

One more embodiment of the present invention relates to the strain MTCC 5130 wherein said strain is effective in enhancing the yield of plant to about 298.5 g/pot herb yield when used alone.

One more embodiment of the present invention relates to the strain MTCC 5130 wherein said strain is effective in enhancing the yield of plant to about 346 g/pot herb yield when used in combination with other bioinoculants.

Yet another embodiment of the present invention relates to the strain MTCC 5130 wherein said strain initiates plant rooting within 20–30 days.

Still another embodiment of the present invention relates to strain MTCC 5130 wherein said strain initiates plant rooting within 22–35 days.

One more embodiment of the present invention relates to strain MTCC 5130 wherein said strain provides 100% survival of plants.

Yet another embodiment of the present invention relates to strain MTCC 5130 wherein said strain lowers the percentage infection on plants is in the range of about 60–90%.

One more embodiment of the present relates to a strain MTCC 5130 wherein said reduction of percentage infection on plants in the range of about 50–70%.

The following examples are given by way of illustration of the present invention and should not be construed to limit the scope of the present invention.

EXAMPLES

Example 1

Isolation of a Novel Bacterial Strain, *Bacillus* spp MTCC-5130

Bacteria were isolated from rhizosphere soil and from root tissue of geranium (cv. Bar bourn) growing in the experimental fields of CIMAP at Lucknow (India).

Rhizospheric soil and root materials were placed in a test tube. Ten volumes of phosphate saline buffer (PSB, pH 7.3; Wollum, 1982) were added and the tube was vortexed for 1 minute. A dilution series ($10^{-1}$ to $10^{-8}$) was made using PSB. One hundred □1 of each dilution was plated onto petri dishes containing PDA. Plates were incubated at 25° C. in a growth chamber.

I. Isolation of MTCC-5130 Strain of the Present Invention from Soil.

The bacterial strain of the present invention was isolated from rhizospheric soil of a geranium plant. The samples were collected randomly from the geranium experimental fields at CIMAP, Lucknow to a depth of 0–2-cm, mixed thoroughly and stored at 5° C. in polythene bags. The representative samples were suspended in phosphate buffered saline (PBS) solution, serially diluted and streaked onto agar medium, with a wire loop. A number of different common agar media were used to culture the bacteria, such as nutrient glucose agar (NDA; Difco, Detroit, Mich.), nutrient-broth yeast extract agar (NBY), and potato dextrose agar (PDA), the recipes for which are provided in Schaad (Schaad, 1988, page 3). Colonies appeared on the medium in about 1–5 days at 25±1° C. in dark. The colonies appearing to be *Bacillus* were sub-cultured on fresh PDA plants. The cultures were later purified by a single spore isolation technique and maintained onto PDA slants at 25° C.

Bacterial Growth Media

All bacterial growth media were prepared using distilled water and sterilized by autoclaving prior to use. All bacterial samples were handled using standard aseptic laboratory techniques to maintain purity.

PDA (Potato-Dextrose-Agar): Potato infusion (200 g/l), dextrose (20 g/l and agar 18 g/l. This medium is available commercially from Hi-Media Laboratory, Difco Co. Potato Dextrose Broth(PDB) was made in the same manner except that agar was omitted.

NA (Nutrient Agar) medium: 3 g/l beef extract, 5 g/l peptic digest of animal tissue and 1.5 g/l agar (HI-Media Laboratory Bombay. India) in distilled water. (pH 6.8).

Delivery medium: The delivery medium comprising vermicompost/sawdust was moistened with water and was sterilized by steam sterilization prior to use. Sterilization was typically performed by autoclaving twice, each time for 60 minutes.

Harvesting of Bacterial Growth

Aliquot of 1.5 L Potato-Dextrose Broth (PDB) dispensed 200 ml each in 500 ml Erlenmeyer flasks was inoculated with 100 ml of stock culture and incubated on shaker with a speed 200 rpm at 25 degree C. for three days. Spores were harvested by centrifugation at 3000 rpm for 10 minutes. Supernatant then decanted off and the concentrated spores suspension was washed and used directly to inoculate delivery medium in the ratio of 1:100. Spores of strain MTCC-5130 were also produced by growing culture for 7–10 days on solid medium (for example on PDA) The spores were harvested from culture in petridishes by scrapping the surface of the agar into distilled water. The suspension of spores in water was mixed directly into the delivery medium.

Fungal Pathogens

The cultures of fungal pathogens were obtained from the infected tissues of various medicinal and aromatic plants. They were maintained onto Potato-Dextrose-Agar or Corn meal-Agar slants under mineral oil at 20.degree. C. in the culture collection of Department of Microbiology and Plant Pathology, CIMAP, Lucknow, India. Pathogenicity of each of the cultures was established on host the under glasshouse conditions.

Example 2

Isolate Characterization and Identification

The strain was characterized morphologically by Gram staining; biochemically by indol test, solvent tolerance test and oxidase test; genetically by randomly amplified polymorphic DNA analysis and 16S rDNA sequencing. All the test together proved that the isolate is a new strain of endospore forming *Bacillus* with close proximity to Gamma proteobacteria.

The isolate identified above as having antifungal activity against wide range of plant pathogenic fungi was further characterized using conventional methods.

The *Bacillus* MTCC-5130 strain of present invention is a Gram positive, spore-forming, aerobic, flagellate bacterium, which exhibits potent antifungal properties against a wide range of plant pathogenic fungi. This strain shows the characteristics of *Bacillus* spp nearer to the species *Bacillus subtilis*.

Morphological Analysis

Different morphological parameters such as size, shape and colony characteristics were studied. The bacterial isolate was found to have spherical colonies about 2–3 mm. in diameter, flattened and mucoid in texture. These were gram positive rods. When the staining for endospore formation was carried out the isolate was found to be forming endospores in the centre of the cells. This isolate was found to be similar to *Bacillus* on the basis of endospore position.

Biochemical Analysis:

Solvent Tolerance Test

The isolate MTCC-5130 showed sensitivity towards chloroform and acetone and insensitivity towards butanol, a characteristic observed in gram positive *Bacillus subtilis* taken as control (Table 1).

TABLE 1

Solvent tolerance test for MTCC-5130

| Solvents | E. coli CA8000) | Bacillus subtilis (MTCC-121) | New isolate MTCC-5130 |
|---|---|---|---|
| Acetone | + | − | − |
| Butanol | + | + | + |
| Chloroform | − | − | − |

Indole Test:

The new isolate was tested for indole production along with *E. coli* as a positive control and was negative for indole production.

Oxidase Test Assay:

The new isolate was analyzed and showed the presence of the enzyme cytochrome oxidase like *Bacillus subtilis* as positive control.

Example 3

16S rDNA Sequence and RAPD Analysis

Isolation of Bacterial Genomic DNA (Mini Prep Method):

Bacterial cells were grown in NB (5 ml) at 28° C., overnight. Culture (1.5 ml.) was centrifuged in microfuge tube at 10,000 rpm for 3 minutes. Pellet was resuspended in 567 □l TE buffer by repeated pipetting. Thirty □l 10% SDS and 3 □l of 20 mg/ml Proteinase K, were added, mixed and incubated for 45–60 min. at 37° C. Hundred □l of 5M NaCl was added and mixed thoroughly. Then 80 □l of CTAB/NaCl solution (CTAB 10% NaCl 0.7 M) was added, mixed and incubated for 10 min. at 65° C. Equal volume of chloroform:Isoamyl alcohol (24:1) was added, mixed and centrifuged to 10,000 rpm for 5 min. The supernatant was transferred to a fresh tube. Equal volume of Phenol:Chloroform:Isoamyl alcohol (25:24:1 saturated with TE pH 8.0) was added, mixed and centrifuged for 5 min. The supernatant was transferred to a fresh tube. Isopropanol (0.6 volume) was added and mixed gently until DNA precipitated. The precipitate was then washed with 1 ml of 70% ethanol. After centrifugation for 5 min. at 10,000 rpm supernatant was discarded and the pellet was dried briefly in a lyophilizer. The pellet was resuspended in 20 µl of autoclaved double distilled water and 2 µl was checked on 0.8% agarose gel for yield and purity.

Partial Sequencing of 16S rDNA

About 25 ng of genomic DNA was amplified following the protocol of MicroSeq 500 Kit procured from Perkin Elmer Applied Bio systems (USA). The amplified product was sequenced using the forward sequencing reaction mix. The DNA sequence was searched for homology using BLAST search engine at NCBI site (ncbi.nlm.nih.gov) and FASTA (ebi.ac.uk). Maximum similarity (E value 2e-11, Score 78) was with Gamma proteobacterium AKB16 16S ribosomal RNA gene, partial sequence (Accession no AY083466.). In the FASTA homology search most of the hits were for *Bacillus* spp in addition to Gamma proteobacteria. The partial rDNA sequencing provided a characteristic 16S rDNA not having complete homology with any bacteria of the database but showed similarity towards Gamma proteobacteria and *Bacillus* spp.

(SEQ ID NO:41)

```
  1  TAATGTCGGT GGTGCGTTCA ACATACGTAA GCTAAGTGGA

AAAGACGGGA ATGCCGTCTT TCGACGCCAA GTGGTGGATG

GGCGAGCAAT ATGCGGGCAA TTCGTTCGCA AGATCGGGAC

AATCTTGGGA AATTGGGGTC AACATTGGAC GGCCGCCCGA

ATTGTACGGC CTAAGATACA AAAGGCGGTC CTGGTCATTA

TCCATAGACG GATTTGTGGT GTACCAGTCA GCCGCCGAGG

CAATGGTCTA TTAAGGTAAA GACGTGCAGT TGATTCGAGA

GGGCGACTGG TTATATCGGG ATCGAGATAA TGTTTAAATC

TTCATGGGAG GTAGTAGCAG GGAACTCCTT TTAACCGATT

AAAGCTCCAT TGAGTAATTT TTTTTCAAGC GACCAAGGCC

CCTCGCTTTC AAAGTCTTTC CCCCCCAGGG AAAAATAAAC

GGTGCCCCAA AACAAGGGGG GGATTTCCGT A 471.
```

Randomly Amplified Polymorphic (RAPD) DNA Analysis

The strain of *Bacillus* spp MTCC-5130 showing morphological characteristics nearer to *Bacillus subtilis* was compared through RAPD with a strain of *Bacillus subtilis* (MTCC 121). Polymerase chain reactions (PCRs) were carried out in 25 □l volume. A reaction tube contained 25 ng of DNA, 0.2 unit of Taq DNA polymerase, 100 □l each of dNTPs, 1.5 mM $MgCl_2$ and 5 p mol of decanucleotide primers. The amplifications were carried out using a thermal cycler (MJ Research, USA). The amplified products were loaded in 1.2% agarose gel containing 0.5 □g $ml^{-1}$ of ethidium bromide and photographed by Polaroid system. The primers used have been listed in Table 2 and Table 3.

Following primers were used in the study:

TABLE 2

MAP primers (Synthesized in the laboratory)

| S. No. | Primer (5 pmole/reaction) | Sequence | SEQ ID NO: |
|---|---|---|---|
| 1. | MAP 01 | 5' GTCCAATGAG 3' | 1 |
| 2. | MAP 02 | 5' AGGATACGTG 3' | 2 |
| 3. | MAP 03 | 5' AAATCGGAGC 3' | 3 |
| 4. | MAP 04 | 5' AAGATAGCGG 3' | 4 |
| 5. | MAP 05 | 5' GGATCTGAAC 3' | 5 |
| 6. | MAP 06 | 5' TTGTCTCAGG 3' | 6 |
| 7. | MAP 07 | 5' GTCCTACTCG 3' | 7 |
| 8. | MAP 08 | 5' GTCCTTAGCG 3' | 8 |
| 9. | MAP 09 | 5' TGCGCGATCG 3' | 9 |
| 10. | MAP 10 | 5' AACGTACGCG 3' | 10 |
| 11. | MAP 11 | 5' GCACGCCGGA 3' | 11 |
| 12. | MAP 12 | 5' CACCCTGCGC 3' | 12 |
| 13. | MAP 13 | 5' CATCCCGAAC 3' | 13 |
| 14. | MAP 14 | 5' GGACTCCACG 3' | 14 |
| 15. | MAP 15 | 5' AGCCTGACGC 3' | 15 |
| 16. | MAP 16 | 5' CTATCGCCGC 3' | 16 |
| 17. | MAP 17 | 5' CGGGATCCGG 3' | 17 |
| 18. | MAP 18 | 5' GCCAATTCCG 3' | 18 |
| 19. | MAP 19 | 5' CCCTGCAGGC 3' | 19 |
| 20. | MAP 20 | 5' CCAAGCTTGC 3' | 20 |

TABLE 3

Primer set - OPO (Procured from Operon Technologies, USA)

| S. No. | Primer (5 pmole/reaction) | Sequence | SEQ ID NO: |
|---|---|---|---|
| 1. | OPO 1 | 5' GGCACGTAAG 3' | 21 |
| 2. | OPO 2 | 5' ACGTAGCGTC 3' | 22 |
| 3. | OPO 3 | 5' CTGTTGCTAC 3' | 23 |
| 4. | OPO 4 | 5' AAGTCCGCTC 3' | 24 |
| 5. | OPO 5 | 5' CCCAGTCACT 3' | 25 |
| 6. | OPO 6 | 5' CCACGGGAAG 3' | 26 |
| 7. | OPO 7 | 5' GACCACTGAC 3' | 27 |
| 8. | OPO 8 | 5' CCTCCAGTGT 3' | 28 |
| 9. | OPO 9 | 5' TCCCACGCAA 3' | 29 |
| 10. | OPO 10 | 5' TCAGAGCGCC 3' | 30 |
| 11. | OPO 11 | 5' GAGAGGAGGT 3' | 31 |
| 12. | OPO 12 | 5' CAGTGCTGTG 3' | 32 |
| 13. | OPO 13 | 5' GTCAGAGTCC 3' | 33 |
| 14. | OPO 14 | 5' AGCAGAGCTC 3' | 34 |
| 15. | OPO 15 | 5' TGGCGTCCTT 3' | 35 |
| 16. | OPO 16 | 5' TCGGCGGTTC 3' | 36 |
| 17. | OPO 17 | 5' GGGTTATGCC 3' | 37 |
| 18. | OPO 18 | 5' CTCGCTATCC 3' | 38 |
| 19. | OPO 19 | 5' GGTGCACGTT 3' | 39 |
| 20. | OPO 20 | 5' ACACACGCTG 3' | 40 |

Analysis with these primers could show 11.1% similarity with the tested *Bacillus subtilis* indicating the possibility of the strain as a different species of *Bacillus* and a new species not having any representation in the public database.

So the strain was resolved to a species of *Bacillus* and named as *Bacillus* spp MTCC-5130 and referred all over the specification in this name.

Example 4

Treatment with *Bacillus* spp MTCC-5130 to Initiate Early Rooting in Geranium Cuttings:

Geranium cuttings treated with *Bacillus* strain MTCC-5130, initiated rooting after 22–25 days of treatment, which was 5–7 days earlier than untreated control cuttings. The results were further compared with IBA treatment and it was confirmed that *Bacillus* spp MTCC-5130 treatment gave better results than IBA. Hundred percent survival was observed when the plants developed from MTCC-5130 treated cuttings were transplanted, while plants of untreated cuttings showed 5–20% mortality depending on the time or period of cutting preparation (Table 4).

TABLE 4

Effect of *Bacillus* spp MTCC-5130 treatment on root initiation and survivality of geranium cuttings

| Treatments & date | Root initiation (days after) | % survivality |  |  |
|---|---|---|---|---|
|  |  | Normal | Two node | Apical |
| Nov. 20, 2001 |  |  |  |  |
| B1 | 25 | 100 | 70.0 | 100.0 |
| IBA | 27 | 100 | 69.2 | 95.8 |
| Control | 32 | 87.5 | 60.0 | 83.3 |
| Dec. 5, 2001 |  |  |  |  |
| B1 | 26 | 100 | 100 | 100.0 |
| IBA | 28 | 100 | 100 | 100.0 |
| Control | 35 | 90 | 90.0 | 95.8 |

B1 = *Bacillus* spp MTCC-5130, IBA = Indole butyric acid

Example 5

Effect of *Bacillus* spp MTCC-5130 on the Growth and Productivity of Geranium Under Glasshouse Conditions.

Effect of *Bacillus* spp MTCC-5130 was tested alone and in different combinations to test their effectiveness on the plant growth and productivity of geranium. It produced 298.5 g/pot herb yield when treated alone. The increase was recorded to be 95% over untreated control (153.1 g/plant). The double combinations, the treatment of present strain of invention with *G. aggregatum* also performed best (310 g/pot) and increased herb yield by 102.9%. In combinations of three bio-inoculants, *G. aggregatum*+*Bacillus* spp.+*Streptomyces* sp. produced 346 g/pot herb yield which was recorded to be 126.2% more than untreated control. Thus, treatment of *Bacillus* spp MTCC-5130 performed effectively with other bio-inoculants in the improvement of the productivity of geranium over untreated control.

Example 6

Antifungal Activity Bioassay:

Screening of Various Strains of *Bacillus/Pseudomonas* to Determine Potential of a their Antagonistic Activity Against Plant Pathogens:

The colonies of bacteria were assayed for antifungal activity. One such assay, referred to herein as a streak test, was conducted by first streaking single colonies of bacterial isolates on PDA. The sample was incubated for about 2–5 days, followed by addition of a plug of fungal pathogen to the previously incubated culture, at a specified distance from the bacterial streaks. The resulting culture was examined for areas in which growth of pathogen was inhibited. *Rhizoctonia solani* was used as representative fungal pathogen for screening antifungal activity of different isolates of B. spp. Few more fungal pathogens, such as *Fusarium, Curvularia, Alternaria*, and *Colletotrichum* against which antifungal activity of different bacterial isolates were assessed further.

During screening as described above resulted in the initial identification of four isolates of *Bacillus* which are capable of promoting plant growth and inhibiting mycelial growth of *Rhizoctonia solani*. The tests were performed on two different media, potato dextrose agar (PDA) and nutrient agar(NA). One isolate designated herein as MTCC-5130 inhibited mycelial growth of *R. solani* by at least 50% in comparison to growth of *R. solani* under control conditions. In additional screening experiments the antagonistic effect of bacterial isolates inhibiting the growth of other plant pathogenic fungi belonging to group of *Fusarium, Helminthosporium, Curvularia, Alternaria*, and *Colletotrichum* evaluated.

*Bacillus/Pseudomonas* strains of different origin were screened for potential antagonistic activity in vitro by following common dual culture technique on PDA, where inocula of test organisms have shown inhibition zone in between colonies of antagonist and pathogen 6-day after inoculation and percent growth inhibition was determined. Based on our results *Bacillus* spp CIMAP B1 was selected as the most potential strain among the tested antagonists. It has also been observed that the bacterial strains produced lytic effect on the mycelia of test plant pathogens (Table 5).

TABLE 5

Screening of different strains of *Bacillus* sp. and *Pseudomonas* sp. showing inhibition zone against plant pathogenic fungi.

| Antagonist Strain | Inhibition zone (in mm) against the growth of | | | | |
|---|---|---|---|---|---|
| | *Colletotrichum acutatum* | *Fusarium oxysporum* | *Curvularia andropogonis* | *Alternaria alternata* | *Rhizoctonia solani* (Pyre.) |
| *Bacillus* spp CIMAP.B1 | 25 | 20 | 32 | 15 | 25 |
| *Bacillus* spp CIMAP.B2 | 32 | 20 | — | 20 | 07 |
| *Bacillus* spp CIMAP.B3 | 20 | 20 | 30 | 15 | — |
| *Bacillus* spp CIMAP.B4 | 12 | 15 | 05 | 15 | 10 |
| *Bacillus* spp CIMAP.B5 | 05 | 07 | — | 11 | 10 |
| *Pseudomonas* sp. Psf$_1$ | 30 | 15 | 12 | 15 | 10 |

*Bacillus* spp. CIMAP B1 = MTCC 5130 [*Bacillus* spp. CIMAP B1 was deposited at the International depository, Institute of Microbial Technology (IMTECH), Chandigarh, India and was given Accession No. MTCC-5130]

Example 8

Characterization of MTCC-5130 Strain

In Vitro Testing of Antagonistic Activity of Strain MTCC-5130

The antagonistic activity of strain *Bacillus* spp MTCC-5130 was tested in vitro by following common dual cultures technique on PDA (Morton D T and N. H. Stroube 1955, Phytopathology 45: 419–420) where inhibition zones in between the colonies of antagonist and pathogen was measured 6 days after inoculation and percent growth inhibition was determined. The newly isolated strain of *Bacillus* spp MTCC-5130 was able to inhibit growth of *Rhizoctonia solani* by 50–55%, *Fusarium oxysporum* by 73%, *Fusarium semitectum* by 68%, *Pythium aphanidermatum* by 20%, *Helminthosporium carbonum* by 55%, *Curvularia andropogonis* by 70%, *Alternaria alternata* by 83%, *Colletotrichum acutatum* by 76%, *Colletotrichum capsici* by 65%, *Colletotrichum. gloeosporiodes* by 58.00%, *Corynespora cassiicola* by 48%, and *Thielavia basicola* by 58% in vitro (Table 6).

TABLE 6

In vitro growth inhibition of fungal phytopathogens of some important medicinal & aromatic plants by the new strain *Bacillus* spp CIMAP-B1

| S. No | Inhibition (%) | Pathogens | Disease | Host |
|---|---|---|---|---|
| 1. | 55.00 | *Rhizoctonia solani*(PyRh1) | Root rot & wilt | Pyrethrum |
| 2. | 52.00 | *Rhizoctonia solani*(GRh1) | Wilt | Geranium |
| 3. | 76.00 | *Colletotrichum acutatum* | Anthracnose | " |
| 4. | 65.00 | *Colletotrichum capsici* | Leaf blight | Indian basil |
| 5. | 58.00 | *Colletotrichum gloeosporiodes* | Leaf spot | Aloe |
| 6. | 50.00 | *Rhizoctonia solani*(OPRh1) | Collar rot | Opium poppy |
| 7. | 20.00 | *Pythium aphanidermatum* | Yellowing | Java citronella |
| 8. | 70.00 | *Curvularia andropogonis* | Leaf blight | Java citronella |
| 9. | 83.00 | *Alternaria alternata* | Leaf spot | Menthol mint |
| 10. | 48.00 | *Corynespora cassiicola* | Leaf blight | " |
| | 73.00 | *Fusarium oxysporum* | Wilt | " |
| 11. | 68.00 | *Fusarium semitectum* | " | " |
| 12. | 55.00 | *Helminthosporium carbonum* | Leaf blight | " |
| 13. | 58.00 | *Thielavia basicola* | Stolon & root rot | " |

Example 9

Inhibition of Spore Germination of Fungal Plant Pathogens by Culture Filtrate of *Bacillus* spp MTCC-5130

The 4-day-old-culture filtrate of *Bacillus* spp MTCC-5130 was evaluated against spore germination inhibition of fungal plant pathogens such as *Alternaria. alternata, Colletotrichum acutatum* and *Colletotrichum capsici*. The results indicated that more than 95% spore germination inhibition was recorded at 80% dilution of culture filtrate. Thus, culture filtrate can be used for the management of diseases caused by these fungi in future (Table 7).

TABLE 7

Effect of *Bacillus* spp CIMAP B1 culture filtrate on the spore germination of plant pathogenic fungi

| CF Conc. (%) | Spore germination (%) after 6 h. | | Inhibition over control (%) | |
| --- | --- | --- | --- | --- |
| | *Alternaria alternata* | *Colletotrichum capsici* | *Alternaria alternata* | *Colletotrichum capsici* |
| 0 (control) | 100 | 100 | — | — |
| 10 | 69 | 68 | 31 | 32 |
| 20 | 59 | 56 | 41 | 44 |
| 80 | 06 | 08 | 94 | 97 |
| 80 | 09 | 05 | 91 | 95 |

Example 10

In Vivo Testing of the *Bacillus* spp CIMAP B1 on *Rhizoctonia solani* Causing Root Rot and Wilt Disease of Pyrethrum.

The pyrethrum seedlings were treated with the strain of *Bacillus* spp MTCC-5130 of the present invention and exposed to the fungal pathogen, *Rhizoctonia solani* causing root rot and wilt disease. Initially they were observed to show growth characteristic similar to the untreated unexposed control plants. Later, seedlings treated with *Bacillus* spp CIMAP-B1 and exposed to the inoculum of fungal pathogen, *Rhizoctonia solani* failed to produce typical symptoms of the disease and also produced plants showing growth characteristics superior to the untreated, unexposed plants. The untreated plant inoculated with *R. solani* produced typical symptoms of the disease (Table 8).

TABLE 8

Influence of *Bacillus* spp MTCC-5130 strain on the root rot & wilt disease of pyrethrum caused by *Rhizoctonia solani*:

| S. NO. | Treatments | Plants Infected (%) | DSI* | Rating of Effectiveness |
| --- | --- | --- | --- | --- |
| 1 | Untreated control | 0.0 | 0 | — |
| 2 | Treated control (*R. solani*) | 100 | 4 | — |
| 3 | B1 + *R. solani* | | | |
| | 21-day-prior | 100 | 4.0 | Non-effective |
| | Simultaneous | 50 | 1.6 | Effective |
| | 5-day-post | 50 | 2.0 | Less Effective |
| 4 | Ridomil-mancozeb♦+ *R. solani* | | | |
| | ♦21-day-prior | 100 | 4.0 | Non-effective |
| | ♦Simultaneous | 50 | 1.5 | Effective |
| | ♦5-day-post | 70 | 2.8 | Less Effective |

B1 = *Bacillus* spp MTCC-5130 strain
*Disease severity index was calculated on 0–4 scales disease rating for scoring root rot and wilt symptoms under epiphytotic conditions in the glashouse wherein 0 = no visible reaction; 1 = infection restricted up to 1 cm length on the collar region; 2 =

The spray of cell free culture filtrate of *Bacillus* spp MTCC-5130 on the foliage of geranium in the commercial fields significantly reduced by fungal infection caused by *Colletotrichum acutatum*. The strain *Bacillus* spp MTCC-5130 of the present invention produce vegetative cells or spores for incorporation into a delivery medium. The composition comprising the vegetative cells and spores of *Bacillus* spp MTCC-5130 and the delivery medium has a long shelf life and is suitable for delivering the antagonist to plants for effective control of fungal phytopathogens.

ADVANTAGES OF THE INVENTION

*Bacillus* spp MTCC-5130 strain is capable of promoting the growth of geranium and pyrethrum and inhibiting the growth of wide range of plant pathogenic fungi including *Rhizoctonia, Fusarium, Pythium, Helminthosporium, Curvularia, Alternaria, Colletotrichum, Corynespora* and *Thielavia* which have been causing different kinds of diseases on agricultural, horticultural and medicinal and aromatic crops. A thorough perusal of review of literature reveals that no such strain of *Bacillus* spp has been obtained. The *Bacillus* spp MTCC-5130 strain has moreover novelty in showing growth promotion activity on plant as exemplified in geranium and pyrethrum and growth inhibition of dark spore pathogenic fungi, which are cosmopolitan in distribution. Therefore, it can be utilized as plant growth promoter as well as biocontrol agent against several plant pathogenic fungi of many important crops. This new strain multiplies on simple delivery medium and is cost effective and can be exploited commercially. It is non hazardous and ecofriendly in nature.

So the present invention pertains to the isolation of a number of rhizobacteria from the soil and identification of a new *Bacillus* spp strain referred to as *Bacillus* spp MTCC-5130. This strain is shown to exhibit strong antagonism towards a wide range of fungal pathogens that cause various kinds of plant diseases such as damping-off, root rot, stem rot, collar rot, twig blight, leaf blight and anthracnose as shown in. As such, this B. spp strain is suitable as biocontrol agent that can be used to protect plants against infection by these fungal pathogens. Thus, B. spp CIMAP B sub.1 strain is useful in methods for reducing the susceptibility of plant to fungi infection. The biologically pure culture of B. spp MTCC-5130 strain is capable of promoting the growth of plant and inhibiting the growth of a wide range of plant pathogenic fungi. This new stain of B. spp., called MTCC-5130 was isolated from the soil of geranium (*Pelargonium graveolens*) planted in the experimental fields of CIMAP, Lucknow, UP, India and is capable of promoting the growth of plant and inhibiting the growth of a wide range of plant pathogenic fungi. The invention also provides information on the characterization of the strain B. spp MTCC-5130 exhibiting unique 16S rDNA sequence. The novel strain of B. spp, B. spp MTCC-5130 has been found to promote the growth of geranium and pyrethrum over untreated control. The novel strain of B. spp, B. spp MTCC-5130, has been found to inhibit growth of *Rhizoctonia solani* by at least 50–55%, *Fusarium oxysporum* by at least 93%, *Fusarium semitectum* by at least 88%, *Pythium aphanidermatum* by at least 20%, *Helminthosporium carbonum* by at least 55%, *Curvularia andropogonis* by at least 70%, *Alternaria alternata* by at least 83%, *Colletotrichum acutatum* by at least 76%, *Colletotrichum capsici* by at least 65%, *Colletotrichum gloeosporiodes* by at least 58.00%, *Corynespora cassiicola* by at least 48%, and *Thielavia basicola* by at least 58% in vitro. The present invention also provides a method for evaluating antifungal activity of B. spp MTCC-5130, in vitro against wide range of fungal pathogens of medicinal and aromatic plants.

REFERENCE CITED

U.S. Patent Documents

| | | | |
|---|---|---|---|
| 4250170 | Feb., 1981 | Kawaguchi et al. | |
| 5047239 | Sep., 1991 | Pusey and Robins | |
| 5049379 | Sep., 1991 | Handelsman et al. | |
| 5061495 | Oct., 1991 | Rossall | |
| 5215747 | Jun., 1993 | Hairston., et al. | 424/93. |
| 5344647 | Sep., 1994 | Rossall. | |
| 5403583 | Apr., 1995 | Liu., et al. | 424/93. |
| 5597565 | Jan., 1997 | Leifert et al. | |
| 5650372 | Jul., 1997 | Branly, et al. | |
| 5753222 | May, 1998 | Marrone, et al. | 424/93. |
| 5780080 | Jul., 1998 | Leifert et al. | 504/117. |
| 6004774 | Dec., 1999 | Marrone, et al. | 435/41. |
| 6245551 | Mar., 1999 | Lehman et al. | 435/252.5 |
| 6291426 | Sep., 2001. | Heins, et al. | |
| 6524998 | Feb., 2003 | Kloepper, et al | |

OTHER REFERENCES

1. Alam et al. (1983), "Leaf blight and leaf spot disease of Java citronella caused by *Curvularia andropogonis*" Indian Phytopath. 36: 480–483
2. Alam et al. (1992), "Lethal yellowing of Java citronella (*Cymbopogon winterianus*) caused by *Pythium aphanidermatum*" Plant Dis 43:10578–1061
3. Alam, et al. (1994), "Collar rot and wilt: a new disease of Java citronella (*Cymbopogon winterianus*) caused by *Fusarium moniliforme* Scheldon" Plant Pathology 43:1057–1061
4. Alam et al. (1996), "Damping-off, a new disease of opium poppy caused by *Pythium dissotocum*" Indian Phytopath. 49:94–97
5. Asaka, O. and Shoda, M., (1996), "Biocontrol of *Rhizoctonia solani* damping-off of tomato with *Bacillus subtilis* RB14" Appl. Environ. Microbiol. 62:4081–4085
6. Baker et al. (1983), "Inhibitory effect of *Bacillus subtilis* on *Uromyces phaseoli* and on development of rust pustules on beans leaves" Phytopathol. 73:1148–1152
7. Bland et al., (1995), "Iturin-A, an antifungal peptide produced by *Bacillus subtilis*" Proc. Plant Growth Regulation Soc. Am. 22.sup.nd:102–107
8. Brenner, D. J. (1984), "Bergey's Manual of Systematic Bacteriology (9th) Edition" (Ed. by Krieg, N. R. & Holt, J. G.) pp. 408–420. Williams and Wilkins, Baltimore
9. Chen et al (2002), "Antagonism to the plant pathogenic fungi of *Bacillus subtilis* B-916 and its exudate Chinese J. Biol. Control 18:45–46
10. Cook C. G. et al., (1987), "Effect of treatment with *Bacillus* species on cotton rot traits, yield and *Phymatotrichum* root rot" Belt wide Cotton Production Research Conferences, Proceedings Jan. 4–8, 1987, Dallas, Tex., pp. 43–45
11. Ferreira et al. (1991), "Biological control of Eutypha lata on grapevine by an antagonistic strain of *Bacillus subtilis*" Phytopathology 81: 283–287
12. Glick, B. R., and Bashan, Y. (1997). Genetic manipulation of plant growth-promoting bacteria to enhance biocontrol of phytopathogens. Biotechnology Advances 15, 353–378.
13. Gueldner, R. C. et al., (1988), "Isolation and Identification of Iturins as Antifungal Peptides in Biological Control of Peach Brown Rot with *Bacillus subtilis*," J. Agric. Food Chem. 36:366–370
14. Hassanein and El-Goorani (1992), "The effect of *Bacillus subtilis* on in vitro growth and pathogenicity of *Agrobacterium tumefaciens*" J. Plant Pathol. 133: 239–246
15. He et al. (1994), "Zwittermycin A. an antifungal and plant protection agent from *Bacillus cereus*" Tetrahedron Lett. 35: 2499–2502
16. Hiraoka et al., (1992), "Characterization of *Bacillus subtilis* RB14, coproducer of peptide antibiotics iturin A and surfactin" J. Gen. Appl. Microbiol. 38:635–640
17. Huang et. al (1993), "Bacterial suppression of basal pod rot and end rot of dry peas caused by *Sclerotinia sclerotiorum*" Can. J. Microbiol. 39: 227–233
18. Islam K. Z. and Nandi, B, (1985), "Control of brown spot of rice by *Bacillus megaterium*" J. Plant Dis. Protect. 92: 241–246
19. Islam K. Z. and Nandi, B. (1985), "Inhibition of some fungal pathogens of hose phylloplane by *Bacillus megaterium*" J. Plant Dis. Protect. 92: 233–240
20. Katz, E. and Demain (1977), "The Peptide Antibiotics of *Bacillus*" Bacteriological Reviews, 41: 449–474
21. Kloepper, J. W. 1993. Plant growth-promoting rhizobacteria as biological control agents. In Soil Microbial Ecology—Applications in Agricultural and Environmental Management, ed. F. B. Metting, Jr., pp. 255–274 (Marcel Dekker, Inc., New York).
22. Korzybski, T. et al. (1978), "Section C: Antibiotic isolated from the genus *Bacillus* (Bacilliaceae)" In: Antibiotics—Origin, nature and properties, American Society for Microbiology, Washington D.C. vol. III, pp. 1519–1661
23. Leifert et al., (1995), "Antibiotic production and biocontrol activity by *Bacillus subtilis* CL 27 and *Bacillus pumilus* CL45" J. Appl. Bacteriol. 78: 97–108
24. Loeffler, W. et al. (1986), "Antifungal Effects of Bacilysin and Fengymycin from *Bacillus subtilis* F-29-3. A Comparison with Activities of Other *Bacillus* Antibiotics" J. Phytopathol. 115:204–213
25. McKeen et al. (1986), "Production and partial characterization of antifungal substances antagonistic to *Monilinia fructicola* from *Bacillus subtilis*" Phytopathology 76:136–139
26. Milner et al. (1996), "Production of Kanosamine by *Bacillus cereus* UW85" Appl. Environ. Microb. 62:3061–3065
27. Osburn et al. (1995), "Effect of *Bacillus cereus* UW85 on the yield of soybean at two field sites in Wisconsin" Am. Phytopathol. Soc. 79(6):551–556
28. Pusey et al. (1988), "Pilot tests and commercial production and application of *Bacillus subtilis* (B-3) of post harvest control of peach brown rot" Plant Dis. 72: 622–626
29. Raupach et al. (1998), "Mixtures of Plant Growth-Promoting Rhizobacteria Enhance Biological Control of Multiple Cucumber Pathogens". Phytopathology. 88:1158–1164
30. Schaad, N. W., Ed. (1988), "Laboratory guide for identification of plant pathogenic bacteria", 2nd Ed., APS Press, Minneapolis, Minn., pp. 23, 60–80.
31. Schroth, M. N., et al. (1983), "In selections from the prokaryotes, a handbook on habitats, isolation and identification of bacteria", (Starr, M. P., Ed.) Springer-Verlag, New York, N.Y.
32. Sattar A. and Alam M. (1993), "*Sclerotinia* collar rot of *Trachyspermum ammi*" Indian J. Plant Pathol. 10: 10–11

33. Sattar et al. (1999), "Collar rot: a new disease of opium poppy caused by *Rhizoctonia solani*" Indian J. Plant Pathol. 17:74–76
34. Sattar et al. (2002), "Anthracnose diseases of geranium caused by *Colletotrichum acutatum* in northern Indian plains" J. Mycol. & Pl. Pathol. 32: 31–34
35. Sholberg et al. (1995), "Biocontrol of post harvest disease of apple using *Bacillus* sp. isolated from stored apples" Can. J. Microbiol. 41: 247–252.
36. Singh, V. and Deverall, B. J. (1984), "*Bacillus subtilis* as a control agent against fungal pathogens of citrus fruit" Trans. Br. Mycol. Soc. 83: 487–490.
37. Stabb et al. (1994), "Zwittermycin A-producing strains of *Bacillus cereus* from diverse soils" Appl. Environ. Microbiol. 60:4404–4412.
38. Tsuge et al., (1995), "Characterization of *Bacillus subtilis* YB8, co producer of lipopeptide surfactin and plipastatin B1" J. Gen. Appl. Microbiol. 41:541–545.
39. Schwinn et al., (1991) "Control with Chemicals" Advances in Plant Pathology: vol. 7: *Phytophthora infestans*, the Cause of Late Blight of Potato, Ingram et al., eds., Academic Press, San Diego. 8:255–266
40. Swinburne et al. (1975), "Production of antibiotics by *Bacillus subtilis* and their effect on fungal colonists of apple leaf scars" Trans. Brit. Mycol. Soc. 65:211–217.
41. United States Environmental Protection Agency (EPA), (1992) "Pesticide Fact Sheet—*Bacillus subtilis* GBO3".
42. Utkhede et al (1986), "In vitro Inhibition of plant pathogens . . . ". Can. J. Microbiol. 32: 963–967
43. Wilson, et al. (1989), "Biological Control of Post harvest Diseases" Annual Review of Phytopathology 27: 425–441
44. Wollum, A. G., (1982) "Cultural Methods for Soil Microorganisms," in Methods of Soil Analysis part 2, Second Edition, American Society of Agronomy/Soil Science Society of America, Madison, Wis., pp. 785
45. Yamada et al., (1990), "Biological activity of antifungal substances produced by *Bacillus subtilis*" J. Pesticide Sci. 15:95–96

The invention claimed is:

1. An isolated *Bacillus* spp bacterial strain having accession number MTCC-5130 on deposit with the Microbial Type Culture Collection & Gene Bank, Institute of Microbial Technology, Chandigarh, India, wherein said strain enhances plant growth and inhibits growth of plant fungal pathogens.

* * * * *

SEQUENCE LISTING

```
<160> NUMBER OF SEQ ID NOS: 41

<210> SEQ ID NO 1
<211> LENGTH: 10
<212> TYPE: DNA
<213> ORGANISM: Artificial Sequence
<220> FEATURE:
<223> OTHER INFORMATION: Primer MAP 01

<400> SEQUENCE: 1
gtccaatgag                                                            10

<210> SEQ ID NO 2
<211> LENGTH: 10
<212> TYPE: DNA
<213> ORGANISM: Artificial Sequence
<220> FEATURE:
<223> OTHER INFORMATION: Primer MAP 02

<400> SEQUENCE: 2
aggatacgtg                                                            10

<210> SEQ ID NO 3
<211> LENGTH: 10
<212> TYPE: DNA
<213> ORGANISM: Artificial Sequence
<220> FEATURE:
<223> OTHER INFORMATION: Primer MAP 03

<400> SEQUENCE: 3
aaatcggagc                                                            10

<210> SEQ ID NO 4
<211> LENGTH: 10
<212> TYPE: DNA
<213> ORGANISM: Artificial Sequence
<220> FEATURE:
<223> OTHER INFORMATION: Primer MAP 04

<400> SEQUENCE: 4
aagatagcgg                                                            10
```

```
<210> SEQ ID NO 5
<211> LENGTH: 10
<212> TYPE: DNA
<213> ORGANISM: Artificial Sequence
<220> FEATURE:
<223> OTHER INFORMATION: Primer MAP 05

<400> SEQUENCE: 5
ggatctgaac                                                                10

<210> SEQ ID NO 6
<211> LENGTH: 10
<212> TYPE: DNA
<213> ORGANISM: Artificial Sequence
<220> FEATURE:
<223> OTHER INFORMATION: Primer MAP 06

<400> SEQUENCE: 6
ttgtctcagg                                                                10

<210> SEQ ID NO 7
<211> LENGTH: 10
<212> TYPE: DNA
<213> ORGANISM: Artificial Sequence
<220> FEATURE:
<223> OTHER INFORMATION: Primer MAP 07

<400> SEQUENCE: 7
gtcctactcg                                                                10

<210> SEQ ID NO 8
<211> LENGTH: 10
<212> TYPE: DNA
<213> ORGANISM: Artificial Sequence
<220> FEATURE:
<223> OTHER INFORMATION: Primer MAP 08

<400> SEQUENCE: 8
gtccttagcg                                                                10

<210> SEQ ID NO 9
<211> LENGTH: 10
<212> TYPE: DNA
<213> ORGANISM: Artificial Sequence
<220> FEATURE:
<223> OTHER INFORMATION: Primer MAP 09

<400> SEQUENCE: 9
tgcgcgatcg                                                                10

<210> SEQ ID NO 10
<211> LENGTH: 10
<212> TYPE: DNA
<213> ORGANISM: Artificial Sequence
<220> FEATURE:
<223> OTHER INFORMATION: Primer MAP 10

<400> SEQUENCE: 10
aacgtacgcg                                                                10

<210> SEQ ID NO 11
<211> LENGTH: 10
<212> TYPE: DNA
<213> ORGANISM: Artificial Sequence
<220> FEATURE:
<223> OTHER INFORMATION: Primer MAP 11
```

<400> SEQUENCE: 11
gcacgccgga                                                                  10

<210> SEQ ID NO 12
<211> LENGTH: 10
<212> TYPE: DNA
<213> ORGANISM: Artificial Sequence
<220> FEATURE:
<223> OTHER INFORMATION: Primer MAP 12

<400> SEQUENCE: 12
caccctgcgc                                                                  10

<210> SEQ ID NO 13
<211> LENGTH: 10
<212> TYPE: DNA
<213> ORGANISM: Artificial Sequence
<220> FEATURE:
<223> OTHER INFORMATION: Primer MAP 13

<400> SEQUENCE: 13
catcccgaac                                                                  10

<210> SEQ ID NO 14
<211> LENGTH: 10
<212> TYPE: DNA
<213> ORGANISM: Artificial Sequence
<220> FEATURE:
<223> OTHER INFORMATION: Primer MAP 14

<400> SEQUENCE: 14
ggactccacg                                                                  10

<210> SEQ ID NO 15
<211> LENGTH: 10
<212> TYPE: DNA
<213> ORGANISM: Artificial Sequence
<220> FEATURE:
<223> OTHER INFORMATION: Primer MAP 15

<400> SEQUENCE: 15
agcctgacgc                                                                  10

<210> SEQ ID NO 16
<211> LENGTH: 10
<212> TYPE: DNA
<213> ORGANISM: Artificial Sequence
<220> FEATURE:
<223> OTHER INFORMATION: Primer MAP 16

<400> SEQUENCE: 16
ctatcgccgc                                                                  10

<210> SEQ ID NO 17
<211> LENGTH: 10
<212> TYPE: DNA
<213> ORGANISM: Artificial Sequence
<220> FEATURE:
<223> OTHER INFORMATION: Primer MAP 17

<400> SEQUENCE: 17
cgggatccgg                                                                  10

<210> SEQ ID NO 18
<211> LENGTH: 10

```
<212> TYPE: DNA
<213> ORGANISM: Artificial Sequence
<220> FEATURE:
<223> OTHER INFORMATION: Primer MAP 18

<400> SEQUENCE: 18
gccaattccg                                                            10

<210> SEQ ID NO 19
<211> LENGTH: 10
<212> TYPE: DNA
<213> ORGANISM: Artificial Sequence
<220> FEATURE:
<223> OTHER INFORMATION: Primer MAP 19

<400> SEQUENCE: 19
ccctgcaggc                                                            10

<210> SEQ ID NO 20
<211> LENGTH: 10
<212> TYPE: DNA
<213> ORGANISM: Artificial Sequence
<220> FEATURE:
<223> OTHER INFORMATION: Primer MAP 20

<400> SEQUENCE: 20
ccaagcttgc                                                            10

<210> SEQ ID NO 21
<211> LENGTH: 10
<212> TYPE: DNA
<213> ORGANISM: Artificial Sequence
<220> FEATURE:
<223> OTHER INFORMATION: OPO 1

<400> SEQUENCE: 21
ggcacgtaag                                                            10

<210> SEQ ID NO 22
<211> LENGTH: 10
<212> TYPE: DNA
<213> ORGANISM: Artificial Sequence
<220> FEATURE:
<223> OTHER INFORMATION: OPO 2

<400> SEQUENCE: 22
acgtagcgtc                                                            10

<210> SEQ ID NO 23
<211> LENGTH: 10
<212> TYPE: DNA
<213> ORGANISM: Artificial Sequence
<220> FEATURE:
<223> OTHER INFORMATION: OPO 3

<400> SEQUENCE: 23
ctgttgctac                                                            10

<210> SEQ ID NO 24
<211> LENGTH: 10
<212> TYPE: DNA
<213> ORGANISM: Artificial Sequence
<220> FEATURE:
<223> OTHER INFORMATION: OPO 4

<400> SEQUENCE: 24
```

-continued aagtccgctc                                                          10

<210> SEQ ID NO 25
<211> LENGTH: 10
<212> TYPE: DNA
<213> ORGANISM: Artificial Sequence
<220> FEATURE:
<223> OTHER INFORMATION: OPO 5

<400> SEQUENCE: 25
cccagtcact                                                          10

<210> SEQ ID NO 26
<211> LENGTH: 10
<212> TYPE: DNA
<213> ORGANISM: Artificial Sequence
<220> FEATURE:
<223> OTHER INFORMATION: OPO 6

<400> SEQUENCE: 26
ccacgggaag                                                          10

<210> SEQ ID NO 27
<211> LENGTH: 10
<212> TYPE: DNA
<213> ORGANISM: Artificial Sequence
<220> FEATURE:
<223> OTHER INFORMATION: OPO 7

<400> SEQUENCE: 27
gaccactgac                                                          10

<210> SEQ ID NO 28
<211> LENGTH: 10
<212> TYPE: DNA
<213> ORGANISM: Artificial Sequence
<220> FEATURE:
<223> OTHER INFORMATION: OPO 8

<400> SEQUENCE: 28
cctccagtgt                                                          10

<210> SEQ ID NO 29
<211> LENGTH: 10
<212> TYPE: DNA
<213> ORGANISM: Artificial Sequence
<220> FEATURE:
<223> OTHER INFORMATION: OPO 9

<400> SEQUENCE: 29
tcccacgcaa                                                          10

<210> SEQ ID NO 30
<211> LENGTH: 10
<212> TYPE: DNA
<213> ORGANISM: Artificial Sequence
<220> FEATURE:
<223> OTHER INFORMATION: OPO 10

<400> SEQUENCE: 30
tcagagcgcc                                                          10

<210> SEQ ID NO 31
<211> LENGTH: 10
<212> TYPE: DNA
<213> ORGANISM: Artificial Sequence

```
<220> FEATURE:
<223> OTHER INFORMATION: OPO 11

<400> SEQUENCE: 31
gagaggaggt                                                          10

<210> SEQ ID NO 32
<211> LENGTH: 10
<212> TYPE: DNA
<213> ORGANISM: Artificial Sequence
<220> FEATURE:
<223> OTHER INFORMATION: OPO 12

<400> SEQUENCE: 32
cagtgctgtg                                                          10

<210> SEQ ID NO 33
<211> LENGTH: 10
<212> TYPE: DNA
<213> ORGANISM: Artificial Sequence
<220> FEATURE:
<223> OTHER INFORMATION: OPO 13

<400> SEQUENCE: 33
gtcagagtcc                                                          10

<210> SEQ ID NO 34
<211> LENGTH: 10
<212> TYPE: DNA
<213> ORGANISM: Artificial Sequence
<220> FEATURE:
<223> OTHER INFORMATION: OPO 14

<400> SEQUENCE: 34
agcagagctc                                                          10

<210> SEQ ID NO 35
<211> LENGTH: 10
<212> TYPE: DNA
<213> ORGANISM: Artificial Sequence
<220> FEATURE:
<223> OTHER INFORMATION: OPO 15

<400> SEQUENCE: 35
tggcgtcctt                                                          10

<210> SEQ ID NO 36
<211> LENGTH: 10
<212> TYPE: DNA
<213> ORGANISM: Artificial Sequence
<220> FEATURE:
<223> OTHER INFORMATION: OPO 16

<400> SEQUENCE: 36
tcggcggttc                                                          10

<210> SEQ ID NO 37
<211> LENGTH: 10
<212> TYPE: DNA
<213> ORGANISM: Artificial Sequence
<220> FEATURE:
<223> OTHER INFORMATION: OPO 17

<400> SEQUENCE: 37
gggttatgcc                                                          10
```

```
<210> SEQ ID NO 38
<211> LENGTH: 10
<212> TYPE: DNA
<213> ORGANISM: Artificial Sequence
<220> FEATURE:
<223> OTHER INFORMATION: OPO 18

<400> SEQUENCE: 38
ctcgctatcc                                                          10

<210> SEQ ID NO 39
<211> LENGTH: 10
<212> TYPE: DNA
<213> ORGANISM: Artificial Sequence
<220> FEATURE:
<223> OTHER INFORMATION: OPO 19

<400> SEQUENCE: 39
ggtgcacgtt                                                          10

<210> SEQ ID NO 40
<211> LENGTH: 10
<212> TYPE: DNA
<213> ORGANISM: Artificial Sequence
<220> FEATURE:
<223> OTHER INFORMATION: OPO 20

<400> SEQUENCE: 40
acacacgctg                                                          10

<210> SEQ ID NO 41
<211> LENGTH: 471
<212> TYPE: DNA
<213> ORGANISM: Bacillus sp.

<400> SEQUENCE: 41
taatgtcggt ggtgcgttca acatacgtaa gctaagtgga aaagacggga atgccgtctt    60
tcgacgccaa gtggtggatg ggcgagcaat atgcgggcaa ttcgttcgca agatcgggac   120
aatcttggga aattggggtc aacattggac ggccgcccga attgtacggc ctaagataca   180
aaaggcggtc ctggtcatta tccatagacg gatttgtggt gtaccagtca gccgccgagg   240
caatggtcta ttaaggtaaa gacgtgcagt tgattcgaga gggcgactgg ttatatcggg   300
atcgagataa tgtttaaatc ttcatgggag gtagtagcag ggaactcctt ttaaccgatt   360
aaagctccat tgagtaattt tttttcaagc gaccaaggcc cctcgctttc aaagtctttc   420 cccccaggg aaaaataaac ggtgccccaa acaaggggg ggatttccgt a              471
```